United States Patent
Wieters et al.

(10) Patent No.: US 11,889,990 B2
(45) Date of Patent: Feb. 6, 2024

(54) ENDOSCOPE AND HEATING DEVICE

(71) Applicant: Olympus Winter & Ibe GmbH, Hamburg (DE)

(72) Inventors: Martin Wieters, Barsbuettel (DE); Sebastian Jungbauer, Hamburg (DE); Sven Pabst, Giekau (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 120 days.

(21) Appl. No.: 17/538,226

(22) Filed: Nov. 30, 2021

(65) Prior Publication Data
US 2022/0175238 A1 Jun. 9, 2022

(30) Foreign Application Priority Data

Dec. 3, 2020 (DE) .......................... 10 2020 132 12

(51) Int. Cl.
*A61B 1/12* (2006.01)
*A61B 1/00* (2006.01)

(52) U.S. Cl.
CPC ............ *A61B 1/128* (2013.01); *A61B 1/0008* (2013.01); *A61B 2562/0271* (2013.01); *A61B 2562/166* (2013.01)

(58) Field of Classification Search
CPC .................. A61B 1/0008; A61B 1/128; A61B 2562/0271; A61B 2562/166; A61B 1/127
See application file for complete search history.

(56) References Cited

U.S. PATENT DOCUMENTS

| 10,285,576 | B2 | 5/2019 | Ide | |
|---|---|---|---|---|
| 2010/0309553 | A1* | 12/2010 | Nagamizu | A61B 1/127 359/512 |
| 2014/0221743 | A1* | 8/2014 | Sugiyama | A61B 1/127 600/109 |
| 2015/0297070 | A1* | 10/2015 | Ide | A61B 1/127 600/109 |
| 2017/0215718 | A1* | 8/2017 | Schan | A61B 1/127 |
| 2018/0192862 | A1 | 7/2018 | Ide | |
| 2018/0353062 | A1* | 12/2018 | Makmel | A61B 1/127 |

FOREIGN PATENT DOCUMENTS

| JP | 2015-198739 A | 11/2015 |
|---|---|---|
| WO | 2020/169297 A1 | 8/2020 |

OTHER PUBLICATIONS

Japanese Office Action dated Dec. 6, 2022 received in 2021-196313.
German Office Action dated Sep. 3, 2021 received in 10 2020 132 120.1.
U.S. Appl. No. 17/430,354.

\* cited by examiner

*Primary Examiner* — Aaron B Fairchild
(74) *Attorney, Agent, or Firm* — Scully, Scott, Murphy & Presser, P.C.

(57) ABSTRACT

An endoscope including: an elongated shaft comprising at least a first shaft tube with a window inserted in its distal end, and an electrical heating device arranged proximate to the window at or in the first shaft tube; wherein the heating device includes a flexible printed circuit board on which a resistive heating element configured as a conductor loop and a temperature sensor are arranged, and a heat-conducting structure connected in a thermally conductive manner to the temperature sensor is applied to the printed circuit board.

22 Claims, 2 Drawing Sheets

ENDOSCOPE AND HEATING DEVICE

CROSS-REFERENCE TO RELATED APPLICATION

The present application is based upon and claims the benefit of priority from DE 10 2020 132 120.1 filed on Dec. 3, 2020, the entire contents of which is incorporated herein by reference.

BACKGROUND

Field

The present disclosure is related to an endoscope having an elongated shaft, comprising at least a first shaft tube with a window inserted in its proximal end, and wherein the endoscope further comprises an electrical heating device, which is arranged in the vicinity of the window at or in the first shaft tube, wherein the heating device comprises a flexible printed circuit board on which a resistive heating element configured as a conductor loop and a temperature sensor are arranged. Furthermore, the present disclosure relates to a corresponding heating device.

Prior Art

Endoscopes have long been used in medicine to examine or treat cavities in the body of a human or animal patient that are difficult to access. For this purpose, endoscopes generally have an elongated shaft with a main body attached to its proximal end, at which the endoscope can be held. At the distal end of the shaft, an objective lens is usually arranged, the image of which is transmitted to the proximal end via an optical or electronic image guide and is made available there by suitable means for viewing and/or evaluation. The distal end of the shaft is usually hermetically sealed by a window to prevent the ingress of dirt or liquids.

The shaft of an endoscope can be flexible or rigid. Rigid shafts are assembled from several shaft tubes arranged one inside the other; they are mainly used in urology, gynecology and laparoscopy.

In laparoscopy, the endoscope is inserted through an artificial access into a patient's abdominal cavity, which is expanded with a gas. Especially at the beginning of a procedure, when the endoscope has a much lower temperature than the gas in the patient's abdominal cavity, condensation of moisture on the window of the endoscope may occur. This may sometimes obstruct the view of the attending physician to such an extent that he has to interrupt the procedure and clean the window.

To avoid such condensation, endoscopes comprising a heating device for the window have been known for some time. By means of the heating device, the window of the endoscope is heated to an elevated temperature even before it is inserted into the patient's abdominal cavity, so that the risk of condensation is significantly reduced.

For corresponding endoscopes, however, there are very high requirements for the control of the heating device, since, on the one hand, a sufficient temperature must be reached to avoid condensation and, on the other hand, regulatory limits regarding the surface temperature of medical instruments must be complied with. The temperature of the window and adjacent sections of the shaft must therefore be maintained within a temperature range of, in some cases, a few Kelvin, for example between 37° C. and 40° C.

For this purpose, the heating devices usually comprise a temperature sensor which is arranged close to the first shaft tube in order to measure its temperature and to control the heating device accordingly. A corresponding endoscope is known, for example, from DE 10 2019 104 489 A1.

An essential prerequisite for reliable temperature control is good thermal contact between the temperature sensor and the shaft tube. However, this proves difficult due to the limited installation space and the necessary electrical insulation.

In the above-mentioned DE 10 2019 104 489 A1, the temperature sensor is embedded in a potting body with a defined contour, with one surface of the potting body resting against the shaft tube. Although this results in a well reproducible thermal contact, the solution is still not optimal.

A distal end of an endoscope shaft 2 of the prior art is shown in FIG. 2. The shaft comprises an outer shaft tube 10 and an inner shaft tube 11. Optical fibers 12 are laid between the outer shaft tube 10 and the inner shaft tube 11, which guide light to the distal end of the shaft 2 to illuminate the field of view of the endoscope 1 and emit it there.

An objective lens 4, which consists of a plurality of optical elements, and an electronic image converter 15 are arranged in the inner shaft tube 11. To protect the objective lens 4 and the image converter 15 from dirt and moisture, the inner shaft tube 11 is hermetically sealed by a window 16.

A heating foil 20 is placed around the inner shaft tube 11, by means of which the distal end of the inner shaft tube 11 and the window 16 can be heated. Close to the window 16, a temperature sensor 21 is provided on the heating foil 20, which is surrounded by a potting body 22 that protects the temperature sensor from damage.

The space between the outer shaft tube 10 and the inner shaft tube 11 is closed off in the distal direction by a potting compound 25.

The heat transfer between the inner shaft tube 11 and the temperature sensor 21 is limited by the potting compound 22 and its small contact surface with the inner shaft tube 11.

SUMMARY

An object is therefore to achieve better thermal conduction between the temperature sensor and the shaft tube in an endoscope of the type in question.

Such object can be achieved by an endoscope having an elongated shaft comprising at least a first shaft tube with a window inserted in its proximal end, and wherein the endoscope further comprises an electrical heating device, which is arranged in the vicinity of the window at or in the first shaft tube, wherein the heating device comprises a flexible printed circuit board on which a resistive heating element configured as a conductor loop and a temperature sensor are arranged, wherein a heat-conducting structure connected in a thermally conductive manner to the temperature sensor is additionally applied to the printed circuit board.

The heat-conducting structure can significantly improve the thermal contact between the temperature sensor and the first shaft tube. At the same time, the quality of the thermal contact is independent of the exact orientation of the flexible printed circuit board and is therefore less susceptible to assembly inaccuracies.

The heat-conducting structure may have a surface facing in the direction of the first shaft tube which is larger, such as at least 10 times larger, or at least 100 times larger, than a surface of the temperature sensor facing in the direction of the first shaft tube. This achieves a high quality of the thermal contact. In this case, the heat-conducting structure may comprise a large area conductor track on the printed circuit board.

In an embodiment of an endoscope, the heat-conducting structure may be part of the conductor tracks for the temperature sensor. In this way, good heat conduction is simultaneously ensured via the electrical contact between the temperature sensor and the heat-conducting structure.

In a further embodiment of an endoscope, between the heat-conducting structure and the heating element on the printed circuit board, a distance of between 0.1 mm and 3 mm, such as between 0.2 mm and 2 mm, such as about 0.5 mm, may be provided. By this means, a "thermal short circuit" can be avoided, in which the temperature sensor would measure the temperature of the heating element itself.

In embodiment, the endoscope may comprise at least a second shaft tube arranged in the first shaft tube, and the heating device may be arranged between the first and second shaft tube. The second shaft tube may be a tube in which an optical system and or video camera is disposed.

The surface of the second shaft tube in the region in which the heating device is arranged may consist of a material which has a lower thermal conductivity value than the material of the first shaft tube. This measure also reduces the risk of a "thermal short circuit" between the heating element and the temperature sensor. In this case, the second shaft tube may be made of the material with the low thermal conductivity value in the relevant area and/or be coated with this material. For example, polyetheretherketone (PEEK) or a ceramics may be used as a material. Likewise, an air gap may be provided between the heating device and the surface of the second shaft tube.

In a further embodiment of an endoscope, the temperature sensor may be thermally insulated on its side facing the second shaft tube. This reduces or completely eliminates any influence of the temperature of the second shaft tube on the measured temperature. The thermal insulation may be implemented as a coating with a non-thermally conductive material, for example with an epoxy resin.

The second shaft tube may have a flattening in the region in which the temperature sensor is arranged. This enables a particularly good and smooth contact of the flexible printed circuit board with the first and second shaft tubes, with the temperature sensor being received in the flattening. At the same time, this prevents the temperature sensor from being subjected to a bending load, which in the worst case could lead to breakage of the sensor.

Such object can be furthermore achieved by a heating device of an endoscope according to the above embodiments. With regard to the advantages and effects achievable thereby, explicit reference is made to what has been said above.

BRIEF DESCRIPTION OF THE DRAWINGS

The embodiments are explained in more detail below by means of some exemplary embodiments. In this regard, the illustrated embodiments merely serve to provide a better understanding of the invention without limiting it, in which.

DETAILED DESCRIPTION

Figure 1:
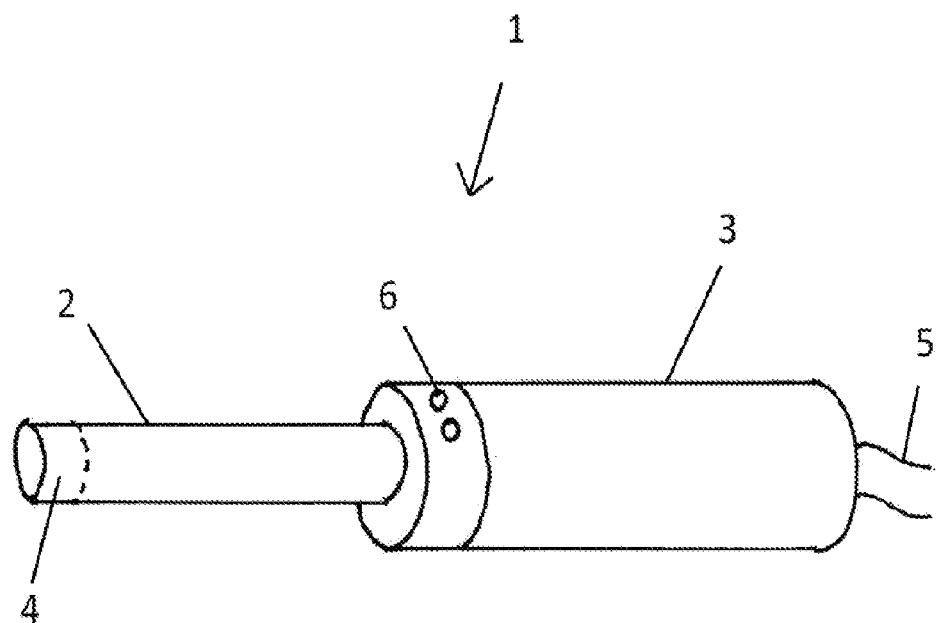
FIG. 1 illustrates an endoscope.
Figure 2:
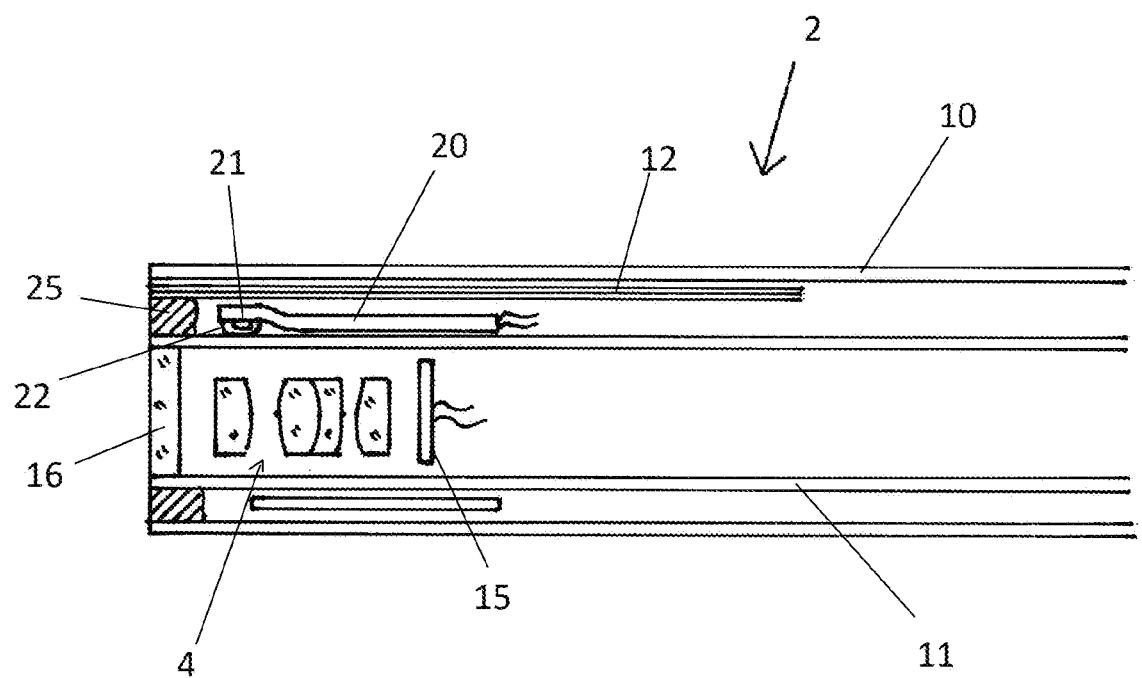
FIG. 2 illustrates the distal end of an endoscope according to the prior art.

FIG. 1 shows an endoscope 1 with an elongated shaft 2 and a main body 3. An objective lens 4 is arranged in the distal end of the shaft 2. The image from the objective lens is converted into electrical video signals by an electronic image converter, not shown, and transmitted to the main body 3. From the main body 3, the video signals are output via a cable 5, if necessary after electronic preprocessing.

Control switches 6 are provided in the distal area of the main body, which can be used to control functions of the endoscope 1 or connected devices. Signals from the operating switches 6 are also routed via the cable 5.

Figure 3:
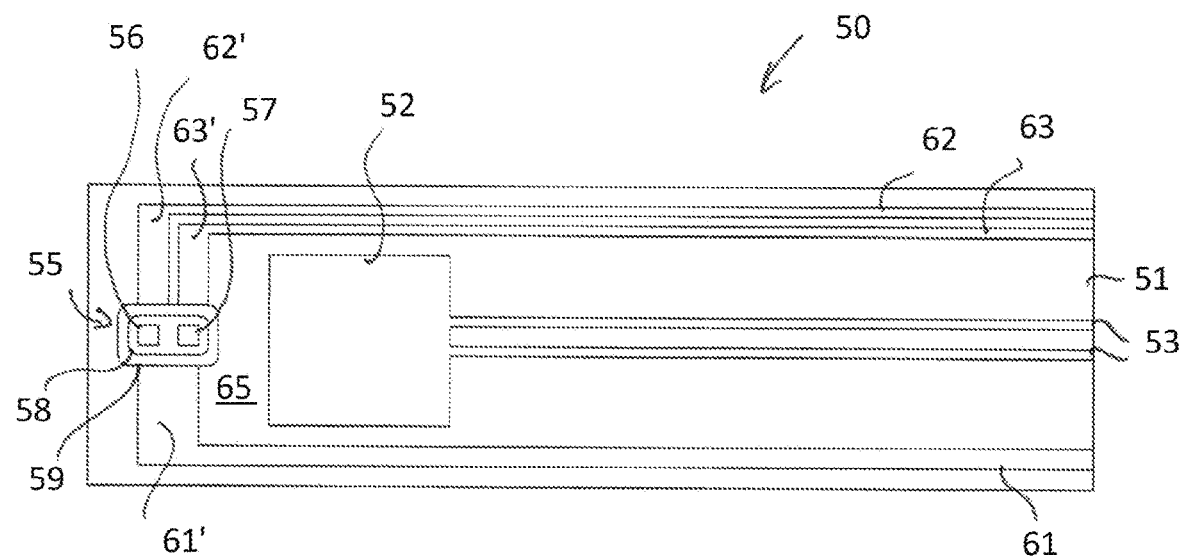
FIG. 3 illustrates a heating device.

FIG. 3 illustrates an improved heating device 50. The heating device 50 comprises a flexible printed circuit board 51 on which a conductor loop 52 is arranged. The exact structure of the conductor loop 52 is not shown for clarity. The conductor loop 52 is supplied with power via supply lines 53.

The heating device 50 further comprises a temperature sensor 55. In the example shown, the temperature sensor 55 comprises two thermistors 56, 57 in a bridge circuit, which are enclosed in a potting body 58 for protection against damage and short circuits. For dimensionally accurate manufacture of the potting body 58, it is molded into a plastic frame 59.

The temperature sensor 50 is connected to an evaluation circuit not shown via conductor tracks 61, 62, 63. In the vicinity of the temperature sensor 50, the conductor tracks 61, 62, 63 are formed over a particularly large area so that they form heat-conducting structures 61', 62', 63'. These heat-conducting structures 61', 62', 63' are connected via the electrical connections, not shown, to the individual thermistors 56, 57 in a heat-conducting manner.

The surface area of the heat-conducting structures 61', 62', 63' is by many times greater than the surface area of the thermistors 56, 57. In FIG. 3, the thermistors 56, 57 and the heat-conducting structures 61', 62', 63' are not shown to scale. For example, the surface area of the heat-conducting structures 61', 62', 63' may be at least 10 times larger than the surface area of the thermistors 56, 57, and the surface area of the heat-conducting structures 61', 62', 63' may even be at least 100 times larger than the surface area of the thermistors 56, 57.

A distance 65 is provided between the conductor loop 52 and the heat-conducting structures 61', 62', 63', which prevents a direct thermal short circuit between the conductor loop 52 and the heat-conducting structures 61', 62', 63'. Depending on the dimensions of the heating device 50, the distance 65 can be at least 1 mm, such as at least 2 mm, or at least 3 mm.

The conductor loop 52, conductor tracks 53, 61, 62, 63 and the heat-conducting structures 61', 62', 63' can be made of a material with good electrical and thermal conductivity. The same material can be used for all elements to simplify manufacturing. Suitable materials are, for example, copper and/or silver.

Figure 4:
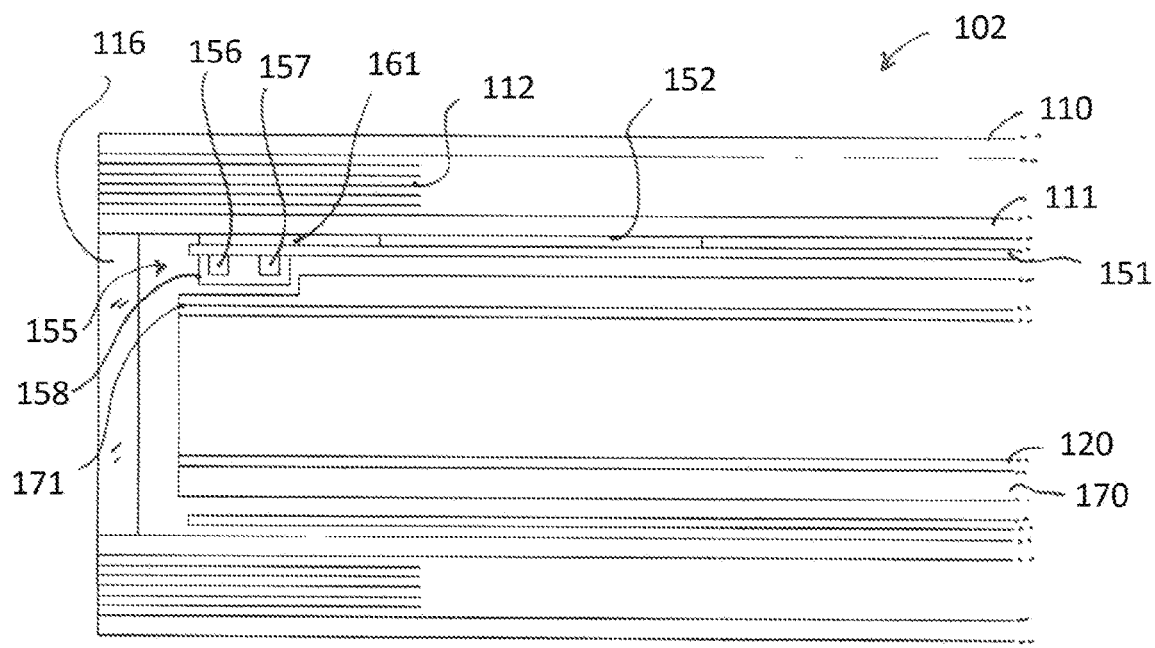
FIG. 4 illustrates the distal end of another endoscope.

FIG. 4 shows the distal end of the shaft 102 of another endoscope. The shaft 102 comprises an outer shaft tube 110 and a middle shaft tube 111, between which optical fibers 112 are arranged. The distal end of the middle shaft tube 111 is hermetically sealed by a window 116.

A further, inner shaft tube 120 is arranged in the middle shaft tube 111, in which optical and/or optoelectronic components of the endoscope, which are not shown, are arranged. The inner shaft tube may be an R-unit of the endoscope.

A heating device is arranged between the central shaft tube 111 and the inner shaft tube 120, which essentially corresponds to the heating device 50 of FIG. 3. The heating device comprises a flexible printed circuit board 151, onto which a conductor loop 152 acting as a resistive heating element is applied.

To control the heating device, it further comprises a temperature sensor 155 having two thermistors 156, 157 enclosed in a potting body 158.

A thermal contact between the thermistors 156, 157 and the middle shaft tube 111 is mainly established via a conductor track 161 with a large surface area, which is part of the conductor tracks for the thermistors 156, 157. Similar to FIG. 3, further conductor tracks for the thermistors 156, 157 may also be configured with a large surface area and thus contribute to improving the thermal contact.

Due to the fact that the thermal contact of the temperature sensor is mainly established via the conductor track 161, the potting body 158 with the thermistors may be arranged on the opposite side of the printed circuit board 151, i.e., here on the inner side. This simplifies a large-area contact of the printed circuit board 151 with the conductor loop 152 and the conductor track 161 on the inner side of the middle shaft tube 111. In order to prevent a short circuit, the conductive structures 152, 161 arranged on the printed circuit board 151 are provided with an insulation layer which is not shown. At the same time, this insulation layer is made as thin as possible so as not to interfere with the heat conduction between the respective structures 152, 161 and the middle shaft tube 111.

The inner shaft tube 120 is covered on its outer side with a thermal insulation layer 170 to avoid direct heat conduction between the conductor loop 152 and the temperature sensor 155. The insulation layer 170 may be a plastic layer, for example made of polyetheretherketone (PEEK), or a ceramic layer. The insulation layer 170 may surround the inner shaft tube 120 only in the area of the heating device, or over a longer section or the entire length. Additionally, or alternatively, an insulating air layer may be provided between the circuit board 151 and the inner shaft tube 120.

It is thus ensured that the thermal resistance of a parasitic heat conduction path from the conductor loop 152 via the inner shaft tube 120 to the temperature sensor 155 is significantly greater than that of a heat conduction path from the conductor loop 152 via the middle shaft tube 111 to the temperature sensor. Thus, the temperature of the middle shaft tube 111 near the window 116 can be accurately measured by the temperature sensor 155 without the measurement being distorted by heat flow through the parasitic heat conduction path.

At its distal end, the inner shaft tube 120 and/or the insulation layer 170 has an indentation or flattening 171 into which the temperature sensor 155 is inserted. In this case, the potting body 158 serves as additional thermal insulation of the thermistors 156, 157 from the inner shaft tube 120.

To mount the endoscope, the flexible printed circuit board 151 can simply be wrapped around the distal end of the inner shaft tube 120 and fixed there by suitable means. This may be done, for example, by sliding a heat shrink tubing over the inner shaft tube 120 and the circuit board 151 outside the area of the conductor loop 152 and the temperature sensor, and then shrinking the tubing. The inner shaft tube 120 is then slid into the middle shaft tube 111 together with the flexible printed circuit board.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An endoscope comprising:
   an elongated shaft comprising at least a first shaft tube with a window inserted in its distal end, and
   an electrical heating device arranged proximate to the window at or in the first shaft tube, wherein the heating device comprises a flexible printed circuit board on which a resistive heating element configured as a conductor loop and a temperature sensor are arranged, and
   a heat-conducting material at least thermally connected to the temperature sensor, the heat-conducting material being applied to the printed circuit board, the heat-conducting material comprising:
      a first portion adjacent to the temperature sensor and elongated in a first direction; and
      a second portion extending from the first portion in a second direction, the second portion being elongated in the second direction;
   wherein a first width of the first portion in a direction perpendicular to the first direction is greater than a second width of the second portion in a direction perpendicular to the second direction.

2. The endoscope according to claim 1, wherein the first portion of the heat-conducting material has a first surface facing the first shaft tube which is larger than a second surface of the temperature sensor facing the first shaft tube.

3. The endoscope according to claim 2, wherein the first surface is at least 10 times larger than the second surface.

4. The endoscope according to claim 2, wherein the first surface is at least 100 times larger than the second surface.

5. The endoscope according to claim 2, wherein the first portion of the heat-conducting material comprises an area of conductor track on the printed circuit board.

6. The endoscope according to claim 1, wherein the first portion of the heat-conducting material is part of conductor tracks for the temperature sensor.

7. The endoscope according claim 1, wherein a distance between the first portion of the heat-conducting material and the heating element on the printed circuit board is between 0.1 mm and 3 mm.

8. The endoscope according to claim 7, wherein the distance is between 0.2 mm and 2 mm.

9. The endoscope according to claim 7, wherein the distance is 0.5 mm.

10. The endoscope according to claim 1, further comprising at least a second shaft tube arranged in the first shaft tube, the heating device being arranged between the first shaft tube and the second shaft tube.

11. The endoscope according to claim 10, wherein a surface of the second shaft tube in a region in which the heating device is arranged comprises a material which has a lower thermal conductivity value than a thermal conductivity of a material of the first shaft tube.

12. The endoscope according to claim 11, wherein an air gap is provided between the heating device and the surface of the second shaft tube.

13. The endoscope according to claim 10, wherein the temperature sensor is thermally insulated on its side facing the second shaft tube.

14. The endoscope according claim 10, wherein the second shaft tube has a flattening in the region in which the temperature sensor is arranged.

15. A heating device for use with an endoscope, the heating device comprising:
- a flexible printed circuit board on which a resistive heating element configured as a conductor loop and a temperature sensor are arranged, and
- a heat-conducting material at least thermally connected to the temperature sensor, the heat-conducting material being applied to the printed circuit board, the heat conducting-material comprising:
  - a first portion adjacent to the temperature sensor and elongated in a first direction; and
  - a second portion extending from the first portion in a second direction, the second portion being elongated in the second direction;
- wherein a first width of the first portion in a direction perpendicular to the first direction is greater than a second width of the second portion in a direction perpendicular to the second direction.

16. The endoscope according to claim 1, wherein the second direction is different from the first direction.

17. The heating device according to claim 15, wherein the second direction is different from the first direction.

18. The endoscope according to claim 1, wherein the heat-conducting material is thermally and electrically connected to the temperature sensor.

19. The heating device according to claim 15, wherein the heat-conducting material is thermally and electrically connected to the temperature sensor.

20. The endoscope according to claim 1, wherein the second direction is a longitudinal direction of the first shaft tube and the first direction is offset from the second direction such that the first and second directions intersect.

21. The heating device according to claim 15, wherein the first direction is offset from the second direction such that the first and second directions intersect.

22. An endoscope comprising:
- an elongated shaft comprising at least a first shaft tube with a window inserted in its distal end, and
- an electrical heating device arranged proximate to the window at or in the first shaft tube, wherein the heating device comprises a flexible printed circuit board on which a resistive heating element configured as a conductor loop and a temperature sensor are arranged, and
- a heat-conducting material at least thermally connected to the temperature sensor, the heat-conducting material being applied to the printed circuit board;
- wherein a distance between the heat-conducting material and the heating element on the printed circuit board is between 0.1 mm and 3 mm.

* * * * *